(12) United States Patent
Fields et al.

(10) Patent No.: US 9,978,479 B2
(45) Date of Patent: *May 22, 2018

(54) ELECTRICALLY ISOLATING POLYMER COMPOSITION

(71) Applicant: Corning Incorporated, Corning, NY (US)

(72) Inventors: Lenwood Lynell Fields, Almond, NY (US); Arthur Winston Martin, Horseheads, NY (US); Shawn Michael O'Malley, Horseheads, NY (US); Dean Michael Thelen, Addison, NY (US)

(73) Assignee: Corning Incorporated, Corning, NY (US)

(*) Notice: Subject to any disclaimer, the term of this patent is extended or adjusted under 35 U.S.C. 154(b) by 58 days.

This patent is subject to a terminal disclaimer.

(21) Appl. No.: 14/546,618

(22) Filed: Nov. 18, 2014

(65) Prior Publication Data

US 2015/0072132 A1 Mar. 12, 2015

Related U.S. Application Data

(60) Continuation-in-part of application No. 13/280,814, filed on Oct. 25, 2011, now Pat. No. 8,920,620, which is a division of application No. 12/393,296, filed on Feb. 26, 2009, now abandoned.

(51) Int. Cl.
| C08F 220/24 | (2006.01) |
| C09D 133/08 | (2006.01) |
| H01B 3/44 | (2006.01) |
| C09D 4/00 | (2006.01) |
| C09D 133/16 | (2006.01) |
| C09D 5/44 | (2006.01) |
| C08F 222/10 | (2006.01) |
| C08G 77/04 | (2006.01) |

(52) U.S. Cl.
CPC ........... H01B 3/447 (2013.01); C08F 220/24 (2013.01); C09D 4/00 (2013.01); C09D 5/44 (2013.01); C09D 133/08 (2013.01); C09D 133/16 (2013.01); C08F 222/1006 (2013.01); C08G 77/045 (2013.01); Y10T 428/31935 (2015.04)

(58) Field of Classification Search
CPC ............. C08F 220/24; C08F 222/1006; C09D 133/08; C09D 133/10; C09D 133/16; C09D 5/44; C09D 4/00
See application file for complete search history.

(56) References Cited

U.S. PATENT DOCUMENTS

| 4,468,432 | A | 8/1984 | Matsukura et al. |
| 5,929,137 | A | 7/1999 | Marsac et al. |
| 6,451,047 | B2 | 9/2002 | McCrea et al. |
| 6,451,947 | B1 * | 9/2002 | Benz ................. H01G 4/18 361/311 |
| 6,761,975 | B1 | 7/2004 | Chen et al. |
| 6,879,861 | B2 | 4/2005 | Benz et al. |
| 8,163,813 | B2 | 4/2012 | Kawaguchi et al. |
| 2004/0097629 | A1 | 5/2004 | Aichele et al. |
| 2006/0084756 | A1 * | 4/2006 | Southwell .......... C08G 18/2885 524/589 |
| 2007/0269747 | A1 | 11/2007 | Bahadur et al. |
| 2008/0225378 | A1 | 9/2008 | Weikert et al. |
| 2009/0103236 | A1 | 4/2009 | Nonaka et al. |
| 2010/0147578 | A1 | 6/2010 | Matsumura et al. |
| 2011/0254408 | A1 * | 10/2011 | Bharti ................ C08F 220/18 310/365 |

FOREIGN PATENT DOCUMENTS

| EP | 0430 722 A2 | 3/1989 |
| EP | 0170913 | 3/1989 |
| EP | 430722 A2 * | 6/1991 |
| JP | 10120611 | 5/1998 |
| JP | 1998120611 | 12/1998 |
| JP | 2007214107 | 8/2007 |
| JP | 2008512281 | 4/2008 |
| WO | 2008155928 | 12/2008 |
| WO | WO 2010077465 A1 * | 7/2010 ............ C08F 220/18 |

OTHER PUBLICATIONS

C.P. Chwang, et al., "Synthesis and characterization of high dielectric constant polyanline/polyurethane blends", Synthetic Metals, vol. 142, 2004, pp. 275-281.
Z.M. Dang, et al., "Dielectric behavior and dependence of percolation threshold on the conductivity of fillers in polymer-semiconductor composites", Applied Physics Letters, vol. 85, No. 1, Jul. 5, 2004, pp. 97-99.
C. Huang, et al., "All-organic dielectric-percolative three-component composite materials with high electromechanical response", Applied Physics Letters, vol. 84, No. 22, May 31, 2004, pp. 4391-4393.
M.K. Kilaru, et al., "Strong charge trapping and bistable electrowetting on nanocomposite fluoropolymer :BaTiO3 dielectrics", Applied Physics Letters, vol. 90, 2007, pp. 212906-1-212906-3.
J. Lu, et al., "High dielectric constant polyaniline/epoxy composites via in situ polymerization for embedded capacitor applications", Polymer, vol. 48, 2007, pp. 1510-1516.
Q.M. Zhang, et al., "An all-organic composite actuator material with a high dielectric constant", Nature, vol. 419, Sep. 19, 2002, pp. 284-287.
Moon, et al., "Low Voltage Electrowetting-On-Dielectric", Journal of Applied Physics, vol. 92, No. 7, (200), pp. 4080-4087.
Chiang et al; "Polymer Composites With High Dielectric Constant" Ferroelectrics, 2002, vol. 275, pp. 1-9.

(Continued)

Primary Examiner — Karuna P Reddy
(74) Attorney, Agent, or Firm — Matthew A. Doscotch

(57) ABSTRACT

An electrode coating composition that includes at least one crosslinkable monomer; at least one hydrophobic monomer; and at least one dielectric constant enhancing agent selected from dielectric enhancing monomers, ferroelectric particulates, and electroactive polymers. Coatings including the polymer of compositions, and articles including electrically isolating layers are also disclosed.

6 Claims, 1 Drawing Sheet

(56) References Cited

OTHER PUBLICATIONS

CN201080019391.1 First Office Action dated Jul. 2, 2013.
EP10707158.1 Office Action dated Mar. 18, 2014.
International Search Report of the International Searching Authority; PCT/US2010/025304; dated Sep. 17, 2010; 9 Pages.
JP2011552139 Notice Grounds for Rejection dated Aug. 6, 2013.
Mugele et al; "Electrowetting: From Basic to Applications"; J. Phys.: Condens. Matter, 17 (2005): R705-R774.
Noda et al; "High Frequency Dielectric Relaxation in Polymers Filled With Ferroelectric Ceramics"; Mat. Res. Soc. Symp. Proc. vol. 698 © 2002 Materials Research Society. 8.1-8.6.
Raj et al; "Composite Dielectrics and Surfactants for Low Voltage Electrowetting Devices"; IEEE. 2007 187-190.
"Rao et al; ""High K Polymer-Ceramic Nano-Composite Development, Characterization, and Modeling for Embedded Capacitor RF Application""; 2001 Electronic Components and Technology Conference".
Seyrat et al; "Amorphous Fluoropolymers as Insulators for Reversible Low-Voltage Electrowetting"; Journal of Applied Physics, vol. 90, No. 3, Aug. 1, 2001, 1383-1386.
TW099105382 Search Report dated Apr. 17, 2013.
McLachlan et al; "AC and DC Percolative Conductivity of Single Wall Carbon Nanotube Polymer Composites"; Journal of Polymer Science, Part B, Polymer Physics 2005. 3273-3287.
Ying-Ling Liu, et al., "Polyhedral oligomeric silsesquioxane nanocomposites exhibiting ultra-low dielectric constants through POSS orientation into lamellar structures", J. Mater. Chem., 2009, 19, 3643-3647.

* cited by examiner

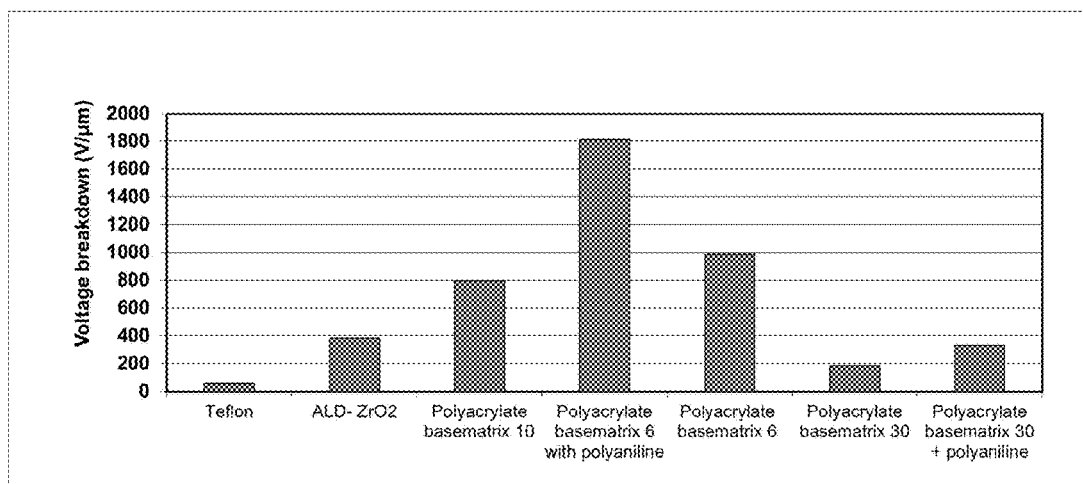

ELECTRICALLY ISOLATING POLYMER COMPOSITION

This application is a continuation-in-part of parent U.S. patent application Ser. No. 12/393,296, filed on Feb. 26, 2009, and divisional U.S. patent application Ser. No. 13/280,814, filed on Oct. 25, 2011, the content of which is relied upon and incorporated herein by reference in its entirety, and the benefit of priority under 35 U.S.C. § 120 is hereby claimed.

BACKGROUND

The disclosure relates to electrically isolating polymer compositions and coatings and articles including the same.

SUMMARY

The disclosure provides a composition that includes at least one crosslinkable monomer; at least one hydrophobic monomer; and at least one dielectric constant enhancing agent selected from the group consisting of: dielectric enhancing monomers, ferroelectric particulates, and electro-active polymers.

The disclosure provides a coating that includes the polymerized product of at least one crosslinkable monomer; at least one hydrophobic monomer; and at least one dielectric constant enhancing agent selected from the group consisting of: dielectric enhancing monomers, ferroelectric particulates, and electro-active polymers.

The disclosure provides an article that includes an electrically isolating layer that includes the polymerized product of at least one crosslinkable monomer; at least one hydrophobic monomer; and at least one dielectric constant enhancing agent selected from the group consisting of: dielectric enhancing monomers, ferroelectric particulates, and electro-active polymers.

BRIEF DESCRIPTION OF THE DRAWINGS

In embodiments of the disclosure:

FIG. 1 shows a comparison of the measured voltage breakdown for highly crosslinked hydrophobic films of the disclosure relative to Teflon® and an inorganic dielectric barrier coating.

DETAILED DESCRIPTION

Embodiments other than those specifically discussed herein are contemplated and may be made without departing from the scope or spirit of the present disclosure. The following detailed description is not limiting. The definitions provided are to facilitate understanding of certain terms frequently used and do not limit the disclosure.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein.

The recitation of numerical ranges by endpoints includes all numbers subsumed within that range (e.g., 1 to 5 includes 1, 1.5, 2, 2.75, 3, 3.80, 4, and 5) and any range within that range.

As used in this specification and the appended claims, the singular forms "a", "an", and "the" encompass embodiments having plural referents, unless the content clearly dictates otherwise. As used in this specification, use of a singular form of a term, can encompass embodiments including more than one of such term, unless the content clearly dictates otherwise. For example, the phrase "adding a solvent" encompasses adding one solvent, or more than one solvent, unless the content clearly dictates otherwise. As used in this specification and the appended claims, the term "or" is generally employed in its sense including "either or both" unless the context clearly dictates otherwise.

"Include," "including," or like terms means encompassing but not limited to, that is, inclusive and not exclusive.

The disclosure provides compositions, coatings including such compositions, and articles including such compositions. Compositions, coatings, and articles including such compositions can have various properties. In embodiments, the compositions can provide a physical barrier for electrode and electronic coatings that have the combined properties of high resistance to water penetration, high voltage breakdown, relatively high dielectric constant, and are highly hydrophobic.

Electrowetting devices commonly utilize both an inorganic film and an upper hydrophobic film to provide barrier protection to electrowetting electrodes. However, such a multilayer barrier has not been able to afford fabrication of devices that are sufficiently robust to withstand electrical breakdown while in direct contact with liquid. The present disclosure provides electrically isolating coatings that also provide a physical barrier for water penetration especially in electrowetting applications.

In embodiments, the disclosure provides compositions that can be pre-polymer compositions or polymeric compositions. A pre-polymer composition is generally a composition that can be polymerized to form a polymeric composition. A pre-polymer composition can include one or more monomers. As used in this specification, monomer generally has the meaning given it by those of skill in the art. Specifically, a monomer is a relatively small molecule that may become chemically bonded to other monomers to form a larger molecule, which can be referred to as a polymer. The process of chemically bonding one or more monomers to one or more other monomers to form a polymer can be referred to as polymerization.

An exemplary composition can include at least one crosslinkable monomer, at least one hydrophobic monomer, and at least one dielectric enhancing agent. A composition can include, for example, one or more than one kind of crosslinkable monomer, one or more than one kind of hydrophobic monomer, and one or more than one kind of dielectric enhancing agent.

A crosslinkable monomer generally refers to a molecule which can be polymerized and can also allow the resulting polymer to be crosslinked at such a monomer. Generally, a crosslink refers to a bond that links one polymer chain to another polymer chain, or a bond that links one portion of a polymer chain to another portion of the same polymer chain. A crosslinkable monomer includes one portion of the molecule that can be polymerized and one portion of the molecule that can form a chemical bond with some other portion of the polymer. The portion of the molecule that can form a chemical bond with some other portion of the polymer (or a different polymer chain) can be referred to as the crosslinkable moiety. Crosslinking can occur, for example, during polymerization or after polymerization.

The crosslinkable moiety can be the same or different than the portion of the molecule that can be utilized to form the polymer (the polymerizable moiety). In embodiments, the crosslinkable moiety can be the same as the polymerizable moiety. In embodiments, the crosslinkable moiety can be different than the polymerizable moiety. A crosslinkable monomer can include one crosslinkable moiety or more than one crosslinkable moiety.

In embodiments, the disclosure provides an electrode coating composition comprising:
a polymerized product of:
   from 5 to 30 wt % of at least one crosslinkable monomer;
   from 20 to 85 wt % of at least one hydrophobic monomer; and at least one dielectric constant enhancing agent in from 2 to 60 wt %, based on the total weight of the coating composition, wherein the one dielectric constant enhancing agent comprises a mixture of an electroactive polymer in from 2 to 20 wt % and a dielectric enhancing monomer in from 10 to 60 wt %, the coating has a dielectric constant of from 1.5 to 10 and has a breakdown voltage property of from 750 to 1,800 volts per micron.

In embodiments, the coating composition can have a breakdown voltage of, for example, from 750 to 1,800 volts per micron, such as 700, 800, 900, 1000, 1100, 1200, 1300, 1400, 1500, 1600, 1700, and 1800 volts per micron, including intermediate values and ranges.

In embodiments, the electroactive polymer can be, for example, polyaniline and can be present, for example, in from 5 to 10 wt %; the dielectric enhancing monomer can be furfuryl methacrylate and can be present, for example, in from 8 to 25 wt %; the at least one hydrophobic monomer has from 6 to 23 carbon atoms and can be present, for example, in from 20 to 85 wt %; and the at least one crosslinkable monomer can be a methacryl polyhedral oligomeric silsesquioxane or an acryl polyhedral oligomeric silsesquioxane and can be present, for example, in from 5% to 30% wt %, based on the total weight of the composition.

In embodiments, the electrode coating can have a thickness, for example, of from 10 nm to 1 mm.

In embodiments, the coating composition when applied to an electrode can have a thickness of, for example, from 10 nm to 1 mm, such as 10 nm, 20 nm, 50 nm, 100 nm, 150 nm, 200 nm, 250 nm, 300 nm, 1 micron, 10 micron, 1 mm, including intermediated values and ranges.

In embodiments, the crosslinkable monomer can be, for example, at least one of the formulas (I) or (II):

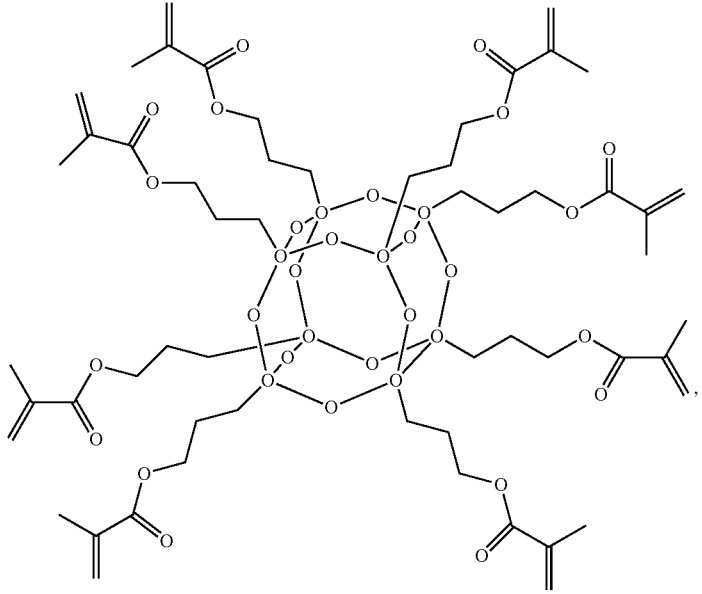

(I)

i.e., a methacryl POSSE' Cage Mixture;

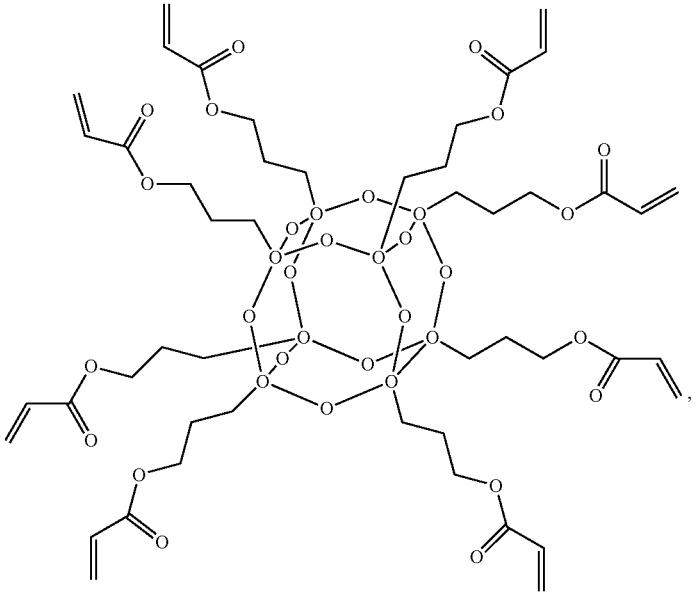

(II)

i.e., an acryl POSS® Cage Mixture, or mixtures thereof.

In embodiments, the coating composition can further comprise, for example, an electroactive polymer in an amount from 2 to 20 wt %, or a combination thereof.

In embodiments, the abovementioned electrode coating composition can have, for example:

the at least one crosslinkable monomer as a dipentaerythritol pentacrylate (CAS 60506-81-2) in from 10 to 30 wt %, e.g., about 20 wt %;

the at least one hydrophobic monomer as a 2,2,3,3,3-pentafluoropropyl acrylate (CAS 356-86-5) in from 45 to 85 wt %, e.g., about 60 wt %; and the at least one dielectric constant enhancing agent as a furfuryl methacrylate (CAS 3454-28-2) in from 10 to 30 wt %, e.g., about 20 wt %. This formulation is an example of the base matrix 10 used in device 10.

In embodiments, this coating composition can have a contact angle of from 110 to 115°.

In embodiments, the coating composition can have, for example:

the at least one crosslinkable monomer as a dipentaerythritol pentacrylate (CAS 60506-81-2) in from 10 to 30 wt %, e.g., about 10 wt %;

the at least one hydrophobic monomer as a 2,2,3,3,4,4,5,5-octafluoropentyl methacrylate (CAS 355-93-1) in from 45 to 85 wt %, e.g., about 80 wt %; and the at least one dielectric constant enhancing agent as a furfuryl methacrylate (CAS 3454-28-2) in from 10 to 30 wt %, e.g., about 10 wt %. This formulation is an example of the base matrix 6 used in device 6. In embodiments, this coating composition can have a contact angle of from 65 to 75°.

In embodiments, the above coating composition or related compositions can further comprise, for example, polyaniline in from 1 to 10 wt % by superaddition.

In embodiments, the above coating composition or related compositions can have, for example:

the at least one hydrophobic monomer as a fluorinated urethane hexacrylate comprising a mixture of 5 to 20 wt % dihydroperfluoropentane having from 40 to 45 wt % acrylic esters and from 40 to 45 wt % urethane hexacrylate, i.e., commercially available as FluorAcryl™ 6975 from Cytonix; and the at least one crosslinkable monomer is a methacryl polyhedral oligomeric silsesquioxane or acryl polyhedral oligomeric silsesquioxanes, e.g., commercially available as an acryl- or methacryl POSS® Cage Mixture from Hybrid Plastics.

In embodiments, the above coating composition or related compositions can further comprise an electroactive polymer in an amount from 2 to 20 wt % by weight.

In embodiments, the disclosure provides an article comprising:

an electrode; and an electrically isolating layer adjacent to and in contact with the electrode, the layer, that is the coating composition, can comprise, for example, the above mentioned polymerized product comprising:

at least one crosslinkable monomer;
at least one hydrophobic monomer; and
at least one dielectric constant enhancing agent selected from the group consisting of: a dielectric enhancing monomer, an electroactive polymer, or a combination thereof.

In embodiments, the article can further comprise, for example, an adhesion promoter disposed between the electrode and the electrically isolating layer.

In embodiments, the article can further comprise, for example, an insulating inorganic layer disposed between the electrode and the electrically isolating layer.

In embodiments, the electrically isolating layer can comprise, for example, two or more layers, for example, 2 to 20 layers. In embodiments, such an interspacer layer can be comprised of, for example, a ceramic, a silica, an amorphous glass, a glass ceramic, or a combination thereof.

In embodiments, the cross-linkable monomer can be at least one of the abovementioned formulas (I) (i.e., a methacryl POSS® Cage Mixture), or (II) (i.e., a acryl POSS® Cage Mixture), or mixtures thereof.

In embodiments, the disclosure provides a method of using the electrode composition, comprising, for example:

disposing the composition on a surface to form a barrier film on the surface; and exposing the barrier film to at least one of:

a single phase fluid, e.g., a gas such as air, or a liquid phase such as water;

a two phase fluid, e.g., a mixture of oil and water;

human skin, e.g., a finger having a differential capacitance compared to the coated electrode;

or a combination thereof.

In embodiments, the surface can be, for example, an electrowetting device. "Electrowetting" and like terms refers to the modification of the wetting properties of a surface, which surface is typically hydrophobic, with an applied electric field.

In embodiments, the surface and barrier film can comprise, for example, a capacitive touch sensor or a fingerprint sensor.

In embodiments, the barrier film mitigates electrostatic discharge (ESD).

In embodiments, disposing the composition on a surface to form a barrier film comprises at least one of:

applying a first coating;

applying a first and a second coating, wherein the first and second coating are the same or different composition;

applying a first coating having a resulting coat having a high breakdown voltage property of from 750 to 1,800 volts per micron;

applying a second coating having a high hydrophobicity property having a high contact angle of from 65° to 114°, or a combination thereof, and where any of the first or second coatings include one or more layers of the first or second coating, for example, 1 to 20 layers or 10 first layers and 10 second layers.

In embodiments, a crosslinkable monomer includes a polymerizable moiety and at least one crosslinkable moiety. A crosslinkable monomer that includes a polymerizable moiety and one crosslinkable moiety can be referred to as a difunctional monomer. In embodiments, a crosslinkable monomer includes a polymerizable moiety and at least two crosslinkable moieties. A crosslinkable monomer that includes a polymerizable moiety and two crosslinkable moieties can be referred to as a trifunctional monomer. In embodiments, a crosslinkable monomer can include a polymerizable moiety having at least three crosslinkable moieties. A crosslinkable monomer that includes a polymerizable moiety and three crosslinkable moieties can be referred to as a tetrafunctional monomer. In embodiments, a crosslinkable monomer can include a polymerizable moiety and at least four crosslinkable moieties. A crosslinkable monomer that includes a polymerizable moiety and four crosslinkable moieties can be referred to as a pentafunctional monomer. In embodiments, a crosslinkable monomer can include a polymerizable moiety and at least five crosslinkable moieties. A crosslinkable monomer that includes a polymerizable moiety and five crosslinkable moieties can be referred to as a hexafunctional monomer.

In embodiments, a crosslinkable monomer can include any type of functional moieties. Exemplary functional moieties include organic moieties such as acrylate moieties, epoxy moieties, urethane moieties, and imide moieties for example. Exemplary functional moieties can also include inorganic moieties, such as siloxane moieties and phosphazene moieties. In embodiments, a crosslinkable monomer can include an acrylate moiety.

In embodiments, a composition can include more than one type of crosslinkable monomer. For example, a composition can include at least two types of crosslinkable monomers. In embodiments, a composition can include one kind of crosslinkable monomer and a hydrophobic monomer that is also crosslinkable (includes a polymerizable moiety and at least one crosslinkable moiety) to modulate the miscibility of the composition. For example, the crosslinkable monomer (or crosslinkable monomers) can be less miscible with the remaining constituents of the composition so a hydrophobic monomer (which is also crosslinkable) can be added to increase the overall miscibility of the composition.

Specific exemplary types of crosslinkable monomers can include, for example, ethoxylated acrylate monomers, such as ethoxylated propane triacrylate monomers and ethoxylated pentaerythritol tetraacrylate. Specific crosslinkable monomers that can be used include, for example, ethoxylated (15) trimethoylol propane triacrylate, ethoxylated (5) trimethoylol propane tetraacrylate, ethoxylated (5) pentaerythritol tetraacrylate, dipentaerythritol pentacrylate, dipentaerythritol hexacrylate, acryl- or methacryl-polyhedral oligomeric silsesquioxane (POSS®), and like monomers, or combinations thereof.

A composition can include various amounts of one or more crosslinkable monomers. Higher amounts of crosslinkable monomers can result in polymers (polymerized compositions) that are more highly crosslinked and therefore are likely to be relatively stiff. In embodiments, a composition can include from about 5% to about 30% of crosslinkable monomer by weight of the total composition (without solvent). In embodiments, a composition can include from about 15% to about 25% of crosslinkable monomer by weight of the total composition (without solvent). In embodiments, a composition can include about 20% of crosslinkable monomer by weight of the total composition (without solvent).

As discussed above, a composition also includes at least one hydrophobic monomer. As used in this specification, hydrophobic generally has the meaning given it by those of skill in the art. Specifically, hydrophobic means antagonistic to water, mostly incapable of dissolving in water in any appreciable amount or being repelled from water. Hydrophobic molecules tend to be nonpolar and thus prefer other neutral molecules and nonpolar solvents. Exemplary hydrophobic molecules include fluorine containing molecules, alkanes, oils, fats, and greasy substances in general.

A hydrophobic monomer can include a polymerizable moiety and at least one hydrophobic moiety, for example a moiety that is non-polar. Exemplary hydrophobic moieties can include, for example, fluorinated moieties or alkyl moieties. In embodiments, a hydrophobic monomer is one that includes five (5) or more fluorine atoms, eight (8) or more fluorine atoms, sixteen (16) or more fluorine atoms, or twenty three (23) or more fluorine atoms. In embodiments, a hydrophobic monomer is one that includes an alkyl chain having at least six (6) carbon atoms, at least twelve (12) carbon atoms, or at least eighteen (18) carbon atoms.

Exemplary specific types of hydrophobic monomers include perfluorinated compounds, or long chain alkyl compounds. Specific exemplary perfluorinated hydrophobic monomers include, for example, pentafluorobenzyl methacrylate; pentafluorophenyl methacrylate; 2,2,3,3,3-pentafluoropropyl acrylate; 2,2,3,3,4,4,5,5-octafluoropentyl methacrylate; 4,4,5,5,6,7,7,7-octafluoro-2-hydroxy-6-(trifluoromethyl)heptyl methacrylate; 2,2,2,3,3,4,4,5,5,6,6,7,7-dodecafluoroheptyl acrylate; 2,2,3,3,4,4,5,5,6,6,7,7,8,8,9,9-hexadecafluorononyl acrylate; 3,3,4,4,5,5,6,6,7,7,8,8,9,9,10,10,11,11,12,12,12-eicosafluorodocecyl acrylate; and combinations thereof. Specific exemplary long chain hydrophobic monomers can include, for example, lauryl methacrylate, stearyl methacrylate, and combinations thereof.

As discussed above, hydrophobic monomers can include a crosslinkable moiety as well. This can be beneficial if the miscibility of the composition is a concern. Exemplary hydrophobic monomers that are also crosslinkable and that may be added to alter the miscibility of the composition include, for example, hexafluoro bisphenol A dimethacrylate; 1H,1H,6H,6H-octafluoro-1,6-hexanediol dimethacrylate; 1H,1H,5H, 5H-hexafluoro-1,4-pentanediol dimethacrylate; pentaerythritol diacrylate monostearate, pentafluorobenzyl methacrylate, pentafluorophenyl methacrylate, and combinations thereof.

In embodiments, a composition can include more than one type of hydrophobic monomer. For example, a composition can include at least two types of hydrophobic monomers (e.g., a hydrophobic monomer and a hydrophobic monomer that is crosslinkable). A monomer that includes a hydrophobic moiety but is crosslinkable (e.g., includes a polymerizable moiety and at least one crosslinkable moiety) is considered a hydrophobic monomer. A composition can include various amounts of one or more hydrophobic monomers. Higher amounts of hydrophobic monomers can result in polymers (polymerized compositions) that are more hydrophobic and can therefore have a higher contact angle with water. In embodiments, a composition can include, for example, from about 20% to about 85% of hydrophobic monomer by weight of the total composition (without solvent). In embodiments, a composition can include, for example, from about 50% to about 80% of hydrophobic monomer by weight of the total composition (without solvent). In embodiments, a composition can include, for example, from about 60% to about 80% of hydrophobic monomer by weight of the total composition (without solvent).

As discussed above, a composition also includes at least one dielectric constant enhancing agent. Dielectric enhancing agents can include, for example, dielectric enhancing monomers, electroactive particles (such as electroactive polymers and conductive nanometal particles), and like agents such as ferroelectric particulates, or a combination thereof. A composition can include one or more than one kind of dielectric enhancing agent, for example, a composition can include one or more than one dielectric enchaining monomer and one or more than one ferroelectric particulate. A composition can include one or more than one particular kind of dielectric enhancing agent, for example, a composition can include at least two dielectric enhancing monomers or at least two dielectric enhancing monomers and one or more than one electroactive polymer.

Dielectric enhancing monomers are monomers that include a polymerizable moiety and a dipole moiety. A dipole moiety generally includes atoms or groups of atoms with opposite electrical charges (full or partial charges) that are separated by an inter-atomic or inter-molecular distance. The polarization strength of the dipole moiety is the result of the group electronegativity. Electronegativity is the tendency of an atom to attract electrons and group electronegativity is the tendency of a polyatomic group to attract electrons. In embodiments, a dielectric enhancing monomer that can be utilized can have a group electronegativity of at least about 2.4. The group electronegativity of a molecule, such as a monomer is a calculated property. The group electronegativity of a monomer can generally be calculated irrespective of its inclusion in a polymer. Illustrative examples include, pentabromophenyl methacrylate (Poly Sciences, Inc., cat. #04253) has a group electronegativity of 3.00; and ethoxylated bisphenol dimethacrylate (Sartomer SR348) has a group electronegativity of 2.74. The group electronegativities of these monomers were calculated using DMol$^3$ (Accelrys Software, Inc., San Diego, Calif.). DMol$^3$ obtained the calculation of the Electron Affinity and Ionization Energy for each molecule. Using these values the group electronegativity was then determined using Mulliken's formula (EA+IE)/2.

Specific types of dielectric enhancing monomers include monomers that contain halogen molecules or monomers that include group (IV) elements, such as zirconium and hafnium. Exemplary monomers that include group (IV) elements include, for example, zirconium acrylate, zirconium bromonorbornanelactone carboxylate triacrylate, zirconium carboxyethyl acrylate 60% (n-propanol), hafnium carboxyethyl acrylate 60% in 1-butanol, and like monomers, or a combination thereof. Other specific exemplary dielectric enhancing monomers include, for example, pentabromophenyl methacrylate, ethoxylated bisphenol dimethacrylate, tris (2-hydroxyethyl) isocyanurate triacrylate, furfuryl methacrylate, benzylmethacrylate, 2-cyanoethylacrylate, vinylferrocene, propagyl methacrylate, and like monomers, or a combination thereof.

In embodiments, a composition can include more than one type of dielectric enhancing monomer. For example, a composition can include at least two types of dielectric enhancing monomers. A monomer that includes a dipole moiety but is crosslinkable (e.g., includes a polymerizable moiety and at least one crosslinkable moiety) is considered a dielectric enhancing monomer. A composition can include various amounts of one or more dielectric enhancing monomers. Higher amounts of dielectric enhancing monomers can result in polymers (polymerized compositions) that have higher dielectric constants and are therefore better electrical isolators. In embodiments, a composition can include, for example, from about 10% to about 60% of dielectric enhancing monomer by weight of the total composition (without solvent). In embodiments, a composition can include, for example, from about 20% to about 60% of dielectric enhancing monomer by weight of the total composition (without solvent).

Ferroelectric particulates can also be selected as a dielectric enhancing agent. Ferroelectric particulates can be used alone as the only dielectric enhancing agent in a composition, or can be used in combination with one or more other dielectric enhancing agents in the composition. Ferroelectric particulates are materials that have high dielectric constants. In embodiments, ferroelectric particulates are materials that have a dielectric constant that is at least about 10, at least about 20, at least about 70, or at least about 160, including intermediate dielectric constant values and ranges.

Exemplary types of ferroelectric particulates can include, for example, titanates, zirconates, and like other inorganic ceramic particles, or a combination thereof. Specific exemplary ferroelectric particulates include barium titanate (BaTiO$_3$), aluminum titanate (AlTiO$_3$), barium zirconate (BaZrO$_3$), alumina (Al$_2$O$_3$), Y$_3$N$_5$O$_{12}$, barium strontium zirconate titanate ("BSZT") ((Ba$_{1-x}$Sr$_x$)(Zr$_x$Ti$_{1-x}$)O$_3$), fullerenes, and like ferroelectric particulates, or a combination thereof.

In embodiments, a composition can include more than one type of ferroelectric particulate. For example, a composition can include at least two types of ferroelectric particulates. A composition can include various amounts of one or more ferroelectric particulates. Higher amounts of ferroelectric particulates can result in polymers (polymerized compositions) that have higher dielectric constants and are superior electrical isolators. In embodiments, a composition can include, for example, from about 5% to about 50% of ferroelectric particulate by weight of the total composition (without solvent). In embodiments, a composition can include from about 20% to about 40% of ferroelectric particulate by weight of the total composition (without solvent).

Electroactive polymers can also be utilized as a dielectric enhancing agent. Electroactive polymers are a class of polymers that can undergo shape changes when a voltage is applied. Electroactive polymers can be classified, for example, as dielectric electroactive polymers or ionic electroactive polymers. In the case of dielectric electroactive polymers the shape deformation can be caused by, for example, electrostatic forces when the polymer is located between two electrodes. For ionic electroactive polymers the shape deformation can be caused by, for example, the displacement of ions within the polymer. Either dielectric electroactive polymers, ionic electroactive polymers, or a combination thereof can be utilized. Electroactive polymers can either be used alone as the only dielectric enhancing agent in a composition or can be used in combination with one or more other dielectric enhancing agents in the composition. For example, a composition can include an electroactive polymer (EAP), and a dielectric enhancing monomer; or a composition could include an EAP, and ferroelectric particulates. In embodiments, electroactive polymers can be materials that have a dielectric constant that is at least about 5.

In embodiments, an electroactive polymer that can be used can have a chemistry that is conjugatable with the monomer components of the composition. This allows the electroactive polymer to be crosslinked into the overall polymer. In embodiments, the electroactive polymers can include pendant hydrophobic functional groups which may aid in dispersion, maintaining the overall hydrophobicity of the films, or both. Exemplary types of electroactive polymers include polythiophenes and polyanilines. Specific exemplary electroactive polymers include conducting polyaniline, copper (II) phthalocyanine, polypyrrole, polyacetylene, polyfluorene, poly(p-phenylene sulfide), polynaphthalene, polytetrathiafulvalene, thiophene polymer ADS 306 PT-EG (American Dye Source, Inc.), and like polymers, or a combination thereof.

In embodiments, a composition can include more than one type of electroactive polymer. For example, a composition can include at least two types of electroactive polymers. A composition can include various amounts of one or more electroactive polymers. Higher amounts of electroactive polymers can result in polymers (polymerized compositions) that have higher dielectric constants and are superior electrical isolators. In embodiments, a composition can include, for example, from about 2% to about 20% of electroactive polymer by weight of the total composition (without solvent), from about 6% to about 20% of electroactive polymer by weight of the total composition (without solvent), or from about 6% to about 10% of electroactive polymer by weight of the total composition (without solvent), including intermediate values and ranges.

A composition can also include other optional components. For example, a composition can include one or more initiators. Both thermal and photoinitiators can be utilized. In embodiments, a photoinitiator can be selected. Exemplary photoinitiators include, the IRGACURE® and DAROCUR® lines of initiators available from Ciba Specialty Chemicals (Basel, Switzerland). In embodiments, where an initiator is selected, the initiator can be used in amounts as commonly known. For example, an initiator can be added in an amount that is from about 1% to about 5% of the total composition (excluding solvent). In embodiments, the initiator can be added in an amount that is about 2% of the total composition (excluding solvent).

Other optional components can also be added to a composition. Such other optional components can include, for example, optical additives such as colorants, dyes, electroluminescent agents, luminescent agents, quantum dots, PDOTs, nano-metal-polymer composites, fluorescently doped silica nanoparticles, stabilizers, and like components, or a combination thereof.

A composition can be formed by combining the monomers with or without additional components, such as solvents. In embodiments, one or more than one monomers can be combined with one or more than one solvent. In embodiments that include relatively more hydrophobic monomer, the conditions (i.e., amount of solvent, order of monomer addition, or other conditions) can be adjusted to maintain the miscibility of the composition. In embodiments, compositions can be formed by combining dielectric enhancing monomer(s) with cross-linkable monomer(s) and then adding hydrophobic monomer(s) either with or without appropriate solvent(s), based, for example, on the identities and amounts of the monomers.

A composition as disclosed herein can be non-polymerized, partially polymerized, or completely polymerized. A composition that is at least partially polymerized can be referred to as a polymeric composition. A composition as disclosed herein can be coated onto a substrate to form a coating or a layer. Generally, a coating of a composition will be polymerized.

A coating of a disclosed composition can be formed as would be known to one of skill in the art, having read this specification. A specific method of forming a coating utilizing a disclosed composition can include a step of obtaining or forming a composition as disclosed above, coating the composition onto a substrate, and curing the composition to form a coating.

The particular coating method that is chosen may depend at least in part on the particular substrate that is being coated, the desired thickness of the coating, other considerations not mentioned herein, or a combination thereof. The particular coating method chosen may also dictate, at least in part whether or not solvent will be added to the composition, and if it is to be added, the quantity of solvent to be added. The particular coating method chosen may also dictate, at least in part whether or not other components will be added to the composition, and if so, the quantity of the components to be added. Specific methods of coating the composition can include, for example, spin coating, dip coating, spray coating, ultrasonic spray coating, vapor coating, electrospinning, knife blade doctoring, wire cater applications, RF magnetron sputtering, extrusion coating, curtain coating, meniscus coating, flexographic deposition, and like methods, or a combination thereof.

The step of curing the composition can be carried out as would be known to one of skill in the art, having read this specification. Exemplary curing methods include, for example, thermal curing, and electromagnetic curing including ultraviolet (UV), visible, microwave, infrared (IR), and like sources of actinic radiation.

Coatings formed from disclosed compositions can afford products having various advantageous properties, including physical barrier to water penetration, high dielectric constant, high voltage breakdown, and like properties, or a combination thereof. Coatings that are effective physical barriers to water penetration can have pin hole free coverage of substrates, high hydrophobicity, a relatively high strength or stiffness, or combinations thereof.

The integrity of a coating can be evaluated using various techniques to observe the micro- or nano-surface of the coating. Exemplary techniques include, for example, scanning electron microscopes (SEM), atomic force microscopy (AFM), ellipsometry, differential scanning calorimetry (DSC), dynamic mechanical analysis (DMA), nano-indentation, Fourier transform infrared spectroscopy (FTIR), and other like forms of optical microscopy. Using such techniques, a coating can be evaluated for numerous properties, including integrity, thermal stability, chemical uniformity, and in some instances the bulk absence of pinholes can be determined Coatings can appear free of pin holes and still be breeched by liquids when voltage is applied. If the disclosed coatings are selected for use in electrowetting applications, pin hole free coatings can be advantageous, as penetration by liquids into the electrowetting display or electrowetting device can short-out the system.

The hydrophobicity of a composition, or a coating formed from a composition can be quantified, for example, by measuring the contact angle of water on a coating of the material. The contact angle is the angle at which a liquid/vapor interface meets the solid surface. Contact angle can be measured using a goniometer. In embodiments, disclosed compositions, once formed into a coating can have a contact angle of at least about 65°, of at least about 90°, at least about 100°, at least about 110°, and at least about 114°, including intermediate values and ranges.

A composition that includes a crosslinkable monomer that has more crosslinkable moieties can result in a polymer that is more highly crosslinked. Alternatively, a composition that includes more crosslinkable monomer compared to a composition that includes less crosslinkable monomer can result in a more highly crosslinked polymer. A polymer that is more highly crosslinked can be stronger than a polymer that is less crosslinked. In embodiments, dynamic mechanical analysis (DMA) can provide a quantitative means for determining the extent of film crosslinking. The amount of crosslinking in a polymer can be evaluated by measuring the crosslinking density of the polymer. The crosslink density of a polymer can be defined as the number of crosslinked monomer units per main chain. Crosslink density (F) can be defined as:

$$\Gamma = \frac{(\overline{M_n})_0}{(\overline{M_n})_c}$$

where $(\overline{M_n})_0$ is the number average molecular weight of uncrosslinked polymer and $(\overline{M_n})_c$ is the number average molecular weight between crosslinks. The higher the crosslink density, the more rigid and generally stronger the polymer. In embodiments, a disclosed polymer can have a crosslink density of at least about 10%, or at least about 20%.

A polymer that is more highly crosslinked can be stiffer than a polymer that is less crosslinked. The stiffness of a polymer can be measured by measuring the elastic modulus of the polymer. An elastic modulus is the description of a substance's tendency to be deformed elastically when a force is applied to it. A particular type of modulus is Young's modulus (E). Young's modulus describes tensile elasticity, or the tendency of a material to deform along an axis when opposing forces are applied along that axis; it is defined as the ratio of tensile stress to tensile strain. Commonly utilized methods of measuring the modulus of a material, such as the Young's modulus of a material can be utilized. The Young's modulus can be measured by nano-indentation, dynamic mechanical analysis, or a combination thereof.

In embodiments, a disclosed coating can have a Young's modulus, for example, of from about 1 MPa to about 200 GPa, or at least about 100 MPa, or at least about 1 GPa.

The disclosed coatings can have the advantage of a relatively high dielectric constant. The dielectric constant (k) of a material is a number relating the ability of the material to carry alternating current compared to the ability of a vacuum to carry alternating current. The dielectric constant of a material can be measured with a test capacitor. The capacitance of the test capacitor with a vacuum between the plates is measured and the capacitance of the test capacitor with the material of interest between the plates is measured. The dielectric constant is the ratio of the capacitance with the test material over the capacitance with a vacuum.

In embodiments, a disclosed coating can have a dielectric constant of at least about 1.5. In embodiments, a disclosed coating can have a dielectric constant of at least about 2. In embodiments, a disclosed coating can have a dielectric constant of at least about 4. In embodiments, a disclosed coating can have a dielectric constant of at least about 7. In embodiments, a disclosed coating can have a dielectric constant of at least about 10.

The disclosed coatings can have the advantage of a relatively high voltage breakdown. The breakdown voltage of a material is the voltage at which the current through the material suddenly increases. Catastrophic breakdown is the voltage at which the material is physically and chemically changed and is accompanied by irreversible damage. Voltage breakdown of a disclosed coating can be measured by using a metal-insulator-metal structure where the disclosed coating is sandwiched between two metallic electrodes. The voltage can be stepwise increased until catastrophic failure occurs. The catastrophic failure can be noted by, for example, arcing, popping, disintegration, or a combination thereof of the dielectric material. Disclosed films can have breakdown voltages as high as 1800 V/μm.

Voltage breakdown levels of various materials can be compared by using an accelerated voltage breakdown protocol. An accelerated breakdown can occur when water is placed in contact with an insulated electrode at relatively high voltage (for example about 125 Volts RMS) and the water penetrates to the electrode over a defined amount of time causing the disclosed coating to breakdown. In embodiments, disclosed coating can have a voltage breakdown of at least about 20 minutes of stability at 120 V, or at least about 40 minutes at 120 V. Under identical conditions TEFLON®, a commonly utilized non-crosslinked hydrophobic polymer, breaks down in 9 seconds.

In embodiments, a coating can also be advantageously utilized in certain applications if it has either a large dielectric constant or a high voltage breakdown. In embodiments, a coating has both a large dielectric constant and a high voltage breakdown. However, a relatively larger dielectric constant can compensate for a lower voltage breakdown. Similarly, a relatively higher voltage breakdown can compensate for a lower dielectric constant.

The disclosed compositions can be useful, for example, in electronic devices, optical devices, or electro-optical devices. A specific type of electro-optical application in which the compositions can be advantageously used is the field of electrowetting and dielectrophoresis. Electrowetting devices are useful in a broad range of applications, including, for example, displays, digital microfluidics, genome DNA sequencing, cell sorting, drug delivery devices, camera image stabilizers, MEMS devices, three dimensional (3D) displays, batteries, projection devices, lenses, reflective displays, sensors, lithographic apparatuses, optical beam splitters, photovoltaics, programmable fluidic processors, touch sensitive devices, micropositioning devices, and chemical microreactors, and like applications, or a combination thereof. Electrowetting technology can be advantageous in display fields, for example, because of its high switching speed, low power consumption, and bright reflective color renditions.

Articles that include the disclosed coated compositions can include, for example, an electrically isolating layer that includes the polymerized product of the compositions disclosed herein. The article can also include other optional components. For example, the electrically isolating layer can be adjacent to an electrode. In embodiments, the electrically isolating layer can be directly adjacent to an electrode. In embodiments, the electrically isolating layer can be disposed on or directly on an electrode. An electrode that can be included in the disclosed articles can be made of, for example, conductive polymers, metals, hybrid materials containing both inorganic and organic conducting agents, semiconductors such as silicon, superconductor materials, and like materials, and a combination thereof.

In embodiments an article can include an adhesion promoter. An adhesion promoter can be disposed between an electrode (or other component) and the electrically isolating layer. Exemplary adhesion promoters include, for example, DYNASYLAN® materials such as DYNASYLAN® Glymo or DYNASYLAN® DAMO-T (Evonik Degussa GmbH, Essen, Germany), and silanes that contain bonding functionalities like acrylates, amines, sulfur, vinyl, or methacrylate group (e.g., glycidoxypropyltrimethoxysilane Z-6040).

Articles can also include multiple coatings formed from the disclosed compositions. Coatings as described herein can also be applied to "free standing" front plane display devices which can be affixed to a backplane.

In embodiments, films or coatings formed from the disclosed compositions can also include surface texture on the coatings. Such nano- or microstructure can further enhance the hydrophobicity of the coating through "Lotus leaf" effects. Similarly, disclosed films or coatings can have hydrophobic materials topically applied to the exposed surface of the coating to further enhance the hydrophobic nature of the coating. In embodiments, micromachining, etching, excimer laser ablation, or combinations thereof can be utilized to introduce surface features onto a film.

Functioning of electrowetting devices are based on the ability of the dielectric film to build up a capacitive charge over the insulating layer to alter the liquid surface interaction. The change in contact angle of the interfacial liquid is directly proportional to the dielectric constant of the film and inversely proportional to the thickness of the dielectric film. For this reason, embodiments can utilize a relatively thin polymeric film having a high dielectric constant.

Advantageous embodiments may include a relatively thin coating that has a relatively large dielectric constant in order to realize as large a capacitance value as possible as seen from the equation for a parallel plate capacitor:

$$C = \frac{\varepsilon_o \varepsilon_r \cdot A}{t}$$

where $\varepsilon_o$ is the permittivity of free space, $\varepsilon_r$ is the material's relative dielectric constant, A is the plate area, and t is the film's thickness. The larger the capacitance, then the smaller the voltage needed to realize the same contact angle. It should be noted that the effective capacitance for capacitors in series is equal to the reciprocal of the sum of the reciprocals of the individual capacitors:

$$C_{eff} = \frac{1}{\frac{1}{C_1} + \frac{1}{C_2} + \ldots + \frac{1}{C_n}}$$

where $C_{eff}$ is the effective capacitance and n is the number of capacitors. This shows that for the polymer film to not limit the capacitance if used with another film, the polymer film should have a capacitance much larger than that of the other film. In embodiments the polymer film can be used as a barrier layer with another layer serving as the hydrophobic film.

The capacitive energy storage is the energy source for the electrowetting actuation. The capacitive energy storage is $$\text{Capacitive Energy} = \frac{1}{2} C_{eff} V^2$$

where V is the applied voltage. When the dielectric constant of a single-layer film is increased by a factor of G, the required applied voltage reduces by a factor of one over the square root of G. The relative dielectric constant of our insulating-material was measured to be about 7, compared to the Teflon® dielectric constant of around 1.9. This corresponds to approximately halving the required voltage.

The disclosed films can be used to make devices which use electrowetting technology. Insulating barrier films having higher dielectric constant and higher voltage breakdown (allowing a thinner film) as described above are known to require less voltage and therefore provide an opportunity to achieve low power consuming reflective displays. Such devices are needed for development of low power consuming reflective displays that rely on electrowetting technology. In addition, the above described films due to their high voltage breakdown can be used to provide digital microfluidics devices which operate at high voltages without failure.

EXAMPLES

Materials and Methods

All chemicals were obtained from Sigma-Aldrich, Milwaukee, Wis. Some of the monomers were obtained from Dajac, Sartomer, American Dye Sources Inc., or Polymer Sciences as well. All monomers and chemicals were used as-is without further purification.

Measurement of Voltage Breakdown. The films were compared to 50 nm (determined via controlled cycling of the atomic layer deposition process) zirconium dioxide inorganic films made through atomic layer deposition (ALD). The voltage breakdown of the films were measured using a sandwich assembly of the film formed on an aluminum electrode with a second aluminum electrode formed on the film. A successive series of AC voltage exposures were applied until film breakdown was visually observed.

Dielectric Constant. The dielectric constant was inferred by combining the thickness of the film (measured using a Zygo white light interferometer (Zygo Corporation, Middlefield, Conn.)) with the capacitance value measured using a LF Impedance Analyzer Model Number HP4192A (Hewlett Packard, Palo Alto, Calif.).

Water Contact Angle. Water contact angles were measured on samples of spin coated glass. Standard contact angle measurements were recorded at 5 different sites on each sample and averaged to obtain a contact angle value. The contact angles were measured on an instrument from Connelly Applied Research (Nazareth, Pa.). Advancing and receding contact angles were also measured using the sessile drop method to successively increase drop size for advancing angles and conversely to decrease drop size for receding contact angles. Each measurement was taken from a different spot on the sample to preserve the water-surface contact angle integrity. The hysteresis was determined for each sample from the data obtained. Hysteresis (H) is the difference between the advancing (θa) and the receding contact angles (θr); H=θa−θr.

Ability to perform droplet actuation via electrowetting and dielectrophoresis. The ability of the films to be used in droplet actuation via a custom voltage addressed electrode device which uses electrowetting and dielectrophoresis was also examined. In this device, a series of pulses A, B, and C are synchronized to individual electrodes that allow a pulsed movement of liquid that is in contact with the electrodes. An empirically determined degree of droplet overhang was needed to allow droplet advancement between the planar electrode pads. The devices in this study were assembled in a sandwich style format, see for example FIG. 25 of Muggle, F. et al., Electrowetting: from basics to applications, *J. Phys.: Condens. Matter*, 17 (2005): R705-R774.

Accelerated failure test via "time-to-hydrolysis" test. This measures the time in which water passes through the film barrier(s) and contacts the electrode to generate gas bubbles at the electrode via hydrolysis. The time in which this failure occurs ("time to hydrolysis") at a given voltage can provide a qualitative visual measure of the failure of the dielectric film barrier. Using the above described sandwich electrode droplet actuation device with a single droplet exposed to an AC voltage of 125 Volts rms, the time required to observe hydrolysis for the disclosed polymer film formulations routinely exceeded TEFLON® by more than a factor of 200.

Examples 1-10

Monomer mixtures were made by combining the monomers listed in Table 1 in the weight percents given for examples 1 through 10. Generally, the mixtures were formed by adding the cross-linkable monomer to the dielectric enhancing monomer and then adding the hydrophobic monomer.

Ten (10) 2.5 inch glass substrates (Eagle XG Glass, 1.1 mm) having an array of aluminum electrodes etched onto their surfaces were then coated with the compositions. The coating was accomplished by applying 1 mL of the solution on the substrate which was then placed over a vacuum retaining spin coating instrument. The solution was then spin coated at 2,500 RPM for 60 seconds with a 5 second ramp rate of 1,800 RPM/sec.

The samples were cured using a "Xenon Model RC-801 high intensity pulsed Ultraviolet (UV) light curing system," which employs a single lamp having a wavelength between 300 to 400 nm. The entire unit was enclosed in a chamber surrounded by a thick red curtain (UV radiation resistant). The chamber housed a purge box that held the substrates and ensured that the substrates were constantly being purged with nitrogen to create an inert environment (for the coatings) during curing. Once the glass substrates were placed in the nitrogen filled purge box, a 60 second purge time was accomplished, and then the UV chamber was closed and the coatings were cured for about 60 seconds. After curing, the substrates were inspected to ensure that they were properly cured. Re-curing was applied if needed to ensure proper curing.

Referring to the FIGURE, FIG. 1 shows a comparison of the measured voltage breakdown for highly crosslinked hydrophobic films of the disclosure relative to Teflon® and an inorganic dielectric barrier coating. The coating compositions and evaluation conditions follow.

Teflon®: The voltage breakdown measurement for Teflon® film was made using 1 micron thick Teflon AF® 2400 (DuPont), which was spin coated over an aluminum electrode on a glass substrate and thermally cured at about 240° C.

ALD-ZrO$_2$: The voltage breakdown for a thin pin hole free inorganic dielectric of zirconia was made using a 50 nm atomic layer deposition (ALD) zirconia ZrO$_2$ film over an aluminum electrode device on a glass substrate. The film was prepared by Cambridge Nanotech, Inc.

Polyacrylate base matrix 10: Polyacrylate base matrix 10 comprised a film of thickness of about 300 to 350 nm. The precursor liquid contained 20 wt % of dipentaerythritol pentacrylate, 60 wt % of 2,2,3,3,3-pentafluoropropyl acrylate, and 20 wt % of furfuryl methacrylate. Approximately 20 to 40 mgs of the photoinitiator IRGACUR® 818 was used per milliliter of the reactants.

Polyacrylate base matrix 10 with polyaniline: This mixture included the above polyacrylate base matrix 10 and 3 wt % by super addition of conducting polyaniline.

Polyacrylate base matrix 6: Polyacrylate base matrix 6 comprised a film of thickness of about 300 to 350 nm. The pre-cursor liquid contained 20 wt % of dipentaerythritol pentacrylate, 60 wt % of 2,2,3,3,4,4,5,5-octafluoropentyl methacrylate, and 20 wt % of furfuryl methacrylate. Approximately 20 to 40 mgs of the photoinitiator IRGACUR® 818 was used per milliliter of the reactants.

Polyacrylate base matrix 6 with polyaniline: This mixture included the above polyacrylate base matrix 6 and 3 wt % by super addition of conducting polyaniline. Polyacrylate base matrix 6 with poly aniline comprised a film of thickness of about 300 to 350 nm.

Polyacrylate base matrix 30: Polyacrylate base matrix 30 was a multi-component monomer mixture containing: 14 wt % hexafluoro bisphenol A dimethacrylate, 14 wt % pentafluorobenzyl methacrylate, 16 wt % dipentaerythritol pentacrylate, 14 wt % furfuryl methacrylate, and 42% of 2,2,3,3,4,4,5,5,6,6,7,7,8,8,9,9-hexadecafluorononyl acrylate. Approximately 20 to 40 mgs of the photoinitiator IRGACUR® 818 was used per milliliter of the reactants.

Polyacrylate base matrix 30 with polyaniline: This mixture included the above polyacrylate base matrix 30 and 3 wt % by super addition of conducting polyaniline. Approximately 20 to 40 mgs of the photoinitiator IRGACUR® 818 was used per milliliter of the reactants.

The monomer percentages for Examples 1 through 10 are shown in Table 1 below.

TABLE 1

| Example Number | Crosslinkable Monomer (wt %) | Hydrophobic Monomer (wt %) | Dielectric Enhancing Monomer (wt %) |
| --- | --- | --- | --- |
| 1 | M200 (20 wt %) | M300 (50 wt %) | M104 (30 wt %) |
| 2 | M200 (10 wt %) | M301 (50 wt %) | M100 (40 wt %) |
| 3 | M200 (5 wt %) | M302 (85 wt %) | M102 (10 wt %) |
| 4 | M200 (10 wt %) | M303 (70 wt %) | M100 (20 wt %) |
| 5 | M201 (10 wt %) | M304 (80 wt %) | M102 (10 wt %) |
| 6 | M202 (10 wt %) | M305 (80 wt %) | M103 (10 wt %) |
| 7 | M201 (20 wt %) | M301 (20 wt %) | M101 (60 wt %) |
| 8 | M201 (20 wt %) | M300 (40 wt %) | M100 (40 wt %) |
| 9 | M201 (25 wt %) | M303 (40 wt %) | M104 (35 wt %) |
| 10 | M202 (20 wt %) | M302 (60 wt %) | M103 (20 wt %) |

M200 = ethoxylated (15) trimethylol propane triacrylate (Sartomer, CN435)
M201 = ethoxylated (5) pentaerythritol tetraacrylate (Sigma-Aldrich, 408263)
M202 = dipentaerythritol pentacrylate (Sigma-Aldrich, 407283)
M300 = 2,2,2,3,3,4,4,5,5,6,6,7,7-dodecafluoroheptyl acrylate (Sigma-Aldrich, 474428)
M301 = 3,3,4,4,5,5,6,6,7,7,8,8,9,9,10,10,11,11,12,12,12-eicosafluorododecyl acrylate (Sigma-Aldrich, 47431-2)
M302 = 2,2,3,3,4,4,5,5-octafluoropentyl methacrylate (Sigma-Aldrich, 470988)
M303 = 2,2,3,3,4,4,5,5,6,6,7,7,8,8,9,9-hexadecafluorononyl acrylate (Sigma-Aldrich, 474436)
M304 = 4,4,5,5,6,7,7-octafluoro-2-hydroxy-6-(trifluoromethyl)heptyl methacrylate (Sigma-Aldrich, 474266)
M305 = 2,2,3,3,3-pentafluoropropyl acrylate (Sigma-Aldrich, 470961)
M100 = pentabromophenyl methacrylate (Poly Sciences, cat. # 04253)
M101 = tris(2-hydroxyethyl)isocyanurate triacrylate (Sartomer Arkema Group, SR368)
M102 = ethoxylated bisphenol dimethacrylate (Sigma-Aldrich, 156329)
M103 = furfuryl methacrylate (Sigma-Aldrich, 411760)
M104 = benzyl methacrylate (Poly Sciences, cat. # 02000)

The contact angles were estimated based on the particular hydrophobic monomer and the amount thereof included in the example. The modulus was estimated based on empirical determinations of other polyacrylate films that were not highly fluorinated but otherwise comparable. The predicted values for examples 1 through 10 are shown in Table 2 below.

TABLE 2

| Example Number | Contact Angle (greater than at least) (°) | Modulus (GPa) | Dielectric Constant |
|---|---|---|---|
| 1 | 100 | 50 | 8.0 |
| 2 | 110 | 25 | 9.0 |
| 3 | 115 | 10 | 4.5 |
| 4 | 120 | 20 | 6.5 |
| 5 | 100 | 5 | 2.1 |
| 6 | 105 | 100 | 2.2 |
| 7 | 100 | 125 | 7.5 |
| 8 | 110 | 100 | 6.5 |
| 9 | 100 | 120 | 3.2 |
| 10 | 100 | 200 | 4.0 |

Example 10 was investigated further. The average standard contact angle was determined as discussed above, to be 71.8°. The average advancing contact angle was measured to be 71.4° and the average receding contact angle was measured to be 68.9°. The hysteresis for the moderately hydrophobic polymer film was 2.5°. In comparison, TEFLON® had a contact angle with water that ranges between 114 to 118° while an inorganic $ZrO_2$ film has a contact angle near 90°. The hydrophobicity of the $ZrO_2$ film surface is significantly reduced over a short time with water contact. This was determined by comparing the decreasing contact angles from the first measured receding contact angle) (78.17° and a measurement made shortly thereafter (64.18°). This suggests that the initial hydrophobicity of some inorganic matrix may not be ideal for those applications requiring consistently high hydrophobicity.

The film of Example 10 was also evaluated as described above for the ability to perform droplet actuation via electrowetting and dielectrophoresis. The film of Example 10 was found to provide droplet actuation.

Example 11

200 mg of hexafluoro bisphenol A dimethacrylate powder (Dajac, cat. #9386) (14% by weight) was dissolved in 0.6 mL acetone and combined with 0.2 ml of pentafluorobenzyl methacrylate (Dajac, cat. #8988) (14% by weight). The mixture was gently heated to 40° C. for about 30 minutes or until fully mixed. Then 0.2 mL of dipentaerythritol penta-/hexa acrylate (Sigma-Aldrich, 407283) (16% by weight) was added to the above mixture and gently vortexed until mixed. Next 0.2 mL of furfuryl methacrylate (14% by weight) was combined and vortexed until mixed. Then 0.6 mL of 2,2,3,3,4,4,5,5,6,6,7,7,8,8,9,9-hexadecafluorononyl acrylate (Sigma-Aldrich, 424266) (42% by weight) was added. A solution of 40 mg of Irgacur 818 in 0.15 ml of N-methylpyrrolidone (NMP) was then added and dissolved into the mixture. The final solution had a clear faintly amber color.

The solution was coated and cured as in Example 1. The contact angle of the film was then measured as in Example 1. The average standard contact angle was determined to be 114.4°. The average advancing contact angle was measured to be 115.5° and the average receding contact angle was measured to be 111.8°. The hysteresis for the high hydrophobic film was 3.7°.

Example 12

Example 10 above was modified by adding polyaniline powder (6 wt % based on the weight of the total composition without the polyaniline). The solution was coated and cured as in Example 1 above. The dielectric constant of the film was then measured as in Example 1 and found to be 7.

The voltage breakdown of this film was also measured and was about 1800 V/micrometer. The breakdown voltage of a 50 nm atomic layer deposition $ZrO_2$ film was found to have an average dielectric breakdown strength of 386 V/micrometer and a TEFLON® film has a reported (and measured) voltage breakdown near about 60 V/micrometer. In addition, the qualitative measurement of the "time-to-hydrolysis" test gave hydrolysis well beyond 30 minutes at 125 V RMS. For comparison, under identical accelerated breakdown voltage tests using a commercially available form of TEFLON® (DuPont) the measured a time-to-hydrolysis was about 9 seconds.

The implementations described above and other implementations are within the scope of the following claims. One skilled in the art will appreciate that the present disclosure can be practiced in embodiments other than those disclosed. The disclosed embodiments are presented for purposes of illustration and not limitation.

What is claimed:

1. An electrode coating composition comprising:
   a polymerized product of:
      from 5 to 30 wt % of at least one crosslinkable monomer selected from a methacryl polyhedral oligomeric silsesquioxane, acryl polyhedral oligomeric silsesquioxane, or a mixture thereof;
      from 20 to 85 wt % of at least one hydrophobic monomer having from 6 to 23 carbon atoms; and
      at least one dielectric constant enhancing agent in from 2 to 60 wt %, based on the total weight of the coating composition,
   wherein the at least one dielectric constant enhancing agent is a mixture of polyaniline in from 5 to 10 wt % and furfuryl methacrylate in from 8 to 25 wt %, and the coating has a dielectric constant of from 1.5 to 10 and has a breakdown voltage property of from 750 to 1,800 volts per micron.

2. An electrode coating composition comprising:
   a polymerized product of:
      from 5 to 30 wt % of at least one crosslinkable monomer of the formula (I), the formula (II), or mixtures thereof;
      from 20 to 85 wt % of at least one hydrophobic monomer; and
      at least one dielectric constant enhancing agent comprised of a mixture of an electroactive polymer in from 2 to 20 wt % and a dielectric constant enhancing monomer in from 10 to 60 wt % based on the total weight of the coating composition,
   wherein, the coating has a dielectric constant of from 1.5 to 10 and has a breakdown voltage property of from 750 to 1,800 volts per micron,

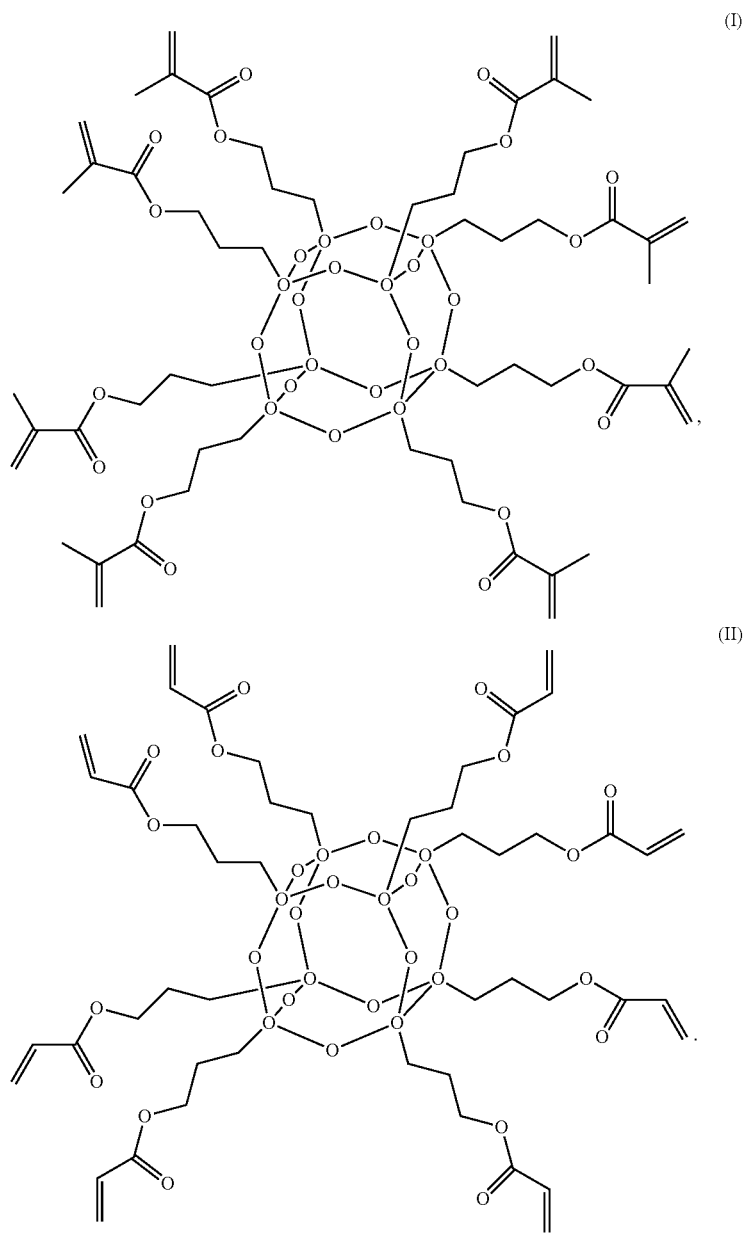

3. The electrode coating composition of claim 2, wherein:
the at least one hydrophobic monomer is 2,2,3,3,3-pentafluoropropyl acrylate in from 45 to 85 wt %; and
the at least one dielectric constant enhancing monomer is furfuryl methacrylate in from 10 to 30 wt %.

4. The electrode coating composition of claim 2, wherein the at least one hydrophobic monomer is 2,2,3,3,4,4,5,5-octafluoropentyl methacrylate in from 45 to 85 wt %; and
the at least one dielectric constant enhancing monomer is furfuryl methacrylate in from 10 to 30 wt %, based on the total weight of the composition.

5. An electrode coating composition comprising:
a polymerized product of:
from 5 to 30 wt % of at least one crosslinkable monomer selected from a methacryl polyhedral oligomeric silsesquioxane or an acryl polyhedral oligomeric silsesquioxane;
from 20 to 85 wt % of at least one hydrophobic monomer consisting of a fluorinated urethane hexacrylate comprised of a mixture of 5 to 20 wt % dihydroperfluoropentane having from 40 to 45 wt % acrylic esters and from 40 to 45 wt % urethane; and
at least one dielectric constant enhancing agent comprised of a mixture of an electroactive polymer in from 2 to 20 wt % and a dielectric enhancing monomer in from 10 to 60 wt %, based on the total weight of the coating composition, wherein the electrode coating has a dielectric constant of from 1.5 to 10 and has a breakdown voltage property of from 750 to 1,800 volts per micron.

6. The electrode coating composition of claim 5 wherein the electroactive polymer is selected from the group consisting of a polythiophene, a polyaniline, a conducting polyaniline, a copper (II) phthalocyanine, a polypyrrole, a polyacetylene, a polyfluorene, a poly(p-phenylene sulfide), a polynaphthalene, a polytetrathiafulvalene, a thiophene polymer, or a combination thereof.

* * * * *

UNITED STATES PATENT AND TRADEMARK OFFICE
CERTIFICATE OF CORRECTION

PATENT NO. : 9,978,479 B2
APPLICATION NO. : 14/546618
DATED : May 22, 2018
INVENTOR(S) : Lenwood Lynell Fields et al.

Page 1 of 3

It is certified that error appears in the above-identified patent and that said Letters Patent is hereby corrected as shown below:

On the Title Page

Column 2, item (56), Line 2, delete "polyanline/polyurethane" and insert
-- polyaniline/polyurethane --, therefor.

Column 2, item (56), Line 13, delete "fluoropolymer :BaTiO3" and insert -- fluoropolymer: BaTiO3 --, therefor.

In the Specification

In Column 1, Line 3-5, delete "12/393,296, filed on Feb. 26, 2009, and divisional U.S. patent application Ser. No, 13/280,814, filed on Oct. 25, 2011," and insert -- 13/280,814, filed on Oct. 25, 2011, which is a divisional U.S. patent application Ser. No, 12/393,296, filed on Feb. 26, 2009, --, therefor.

Signed and Sealed this
Twenty-eighth Day of January, 2020

Andrei Iancu
*Director of the United States Patent and Trademark Office*

CERTIFICATE OF CORRECTION (continued)
U.S. Pat. No. 9,978,479 B2

In the Claims

Column 21, Line 1-50, Claim 2, delete " 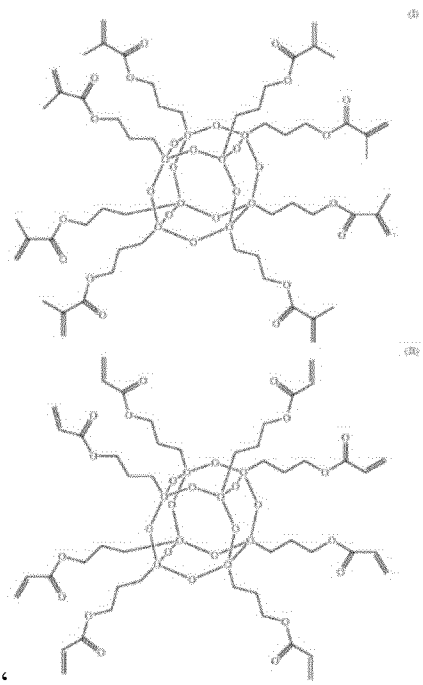 " and insert

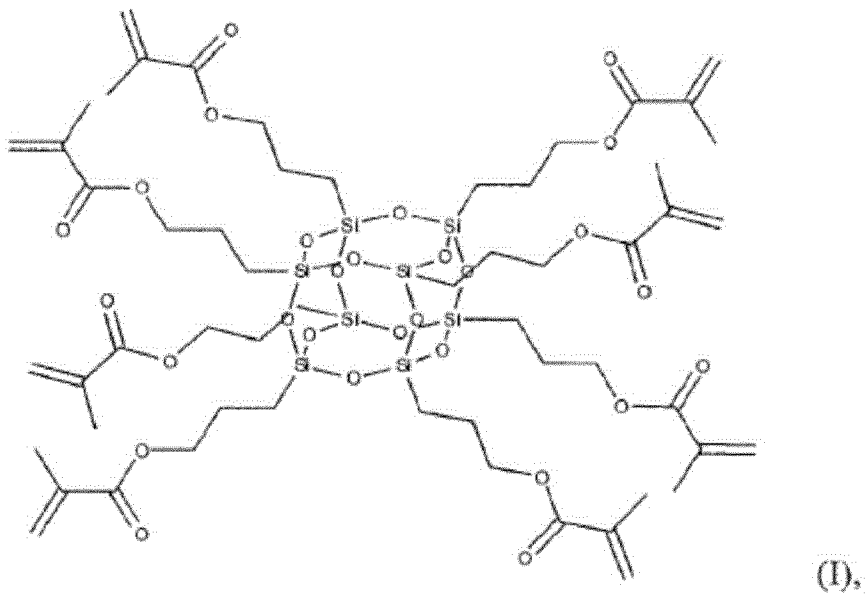

(I), --

CERTIFICATE OF CORRECTION (continued)
U.S. Pat. No. 9,978,479 B2

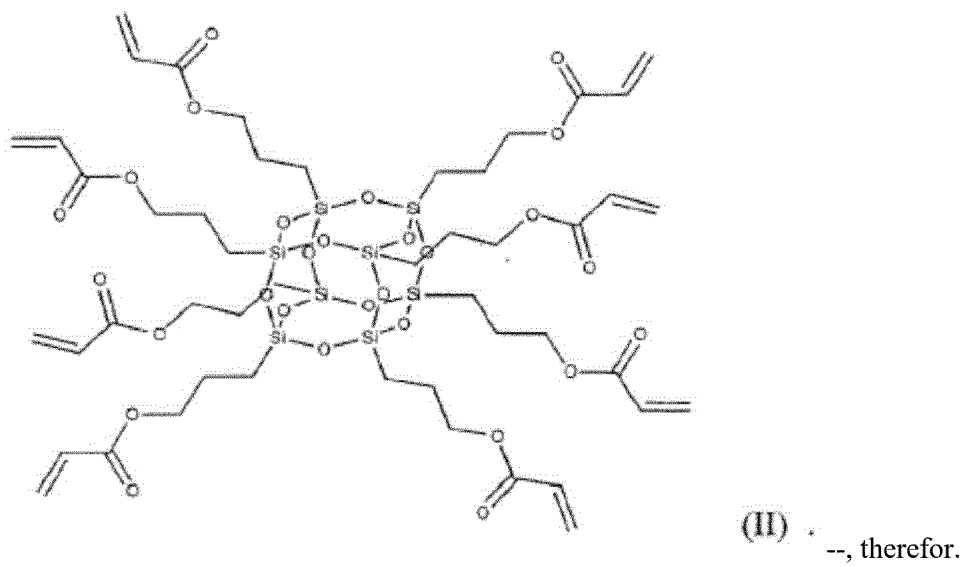

(II) --, therefor.

In Column 22, Line 53, Claim 5, delete "hexacrylate" and insert -- hexaacrylate --, therefor.